US007115132B2

United States Patent
Errico et al.

(10) Patent No.: US 7,115,132 B2
(45) Date of Patent: Oct. 3, 2006

(54) STATIC TRIALS AND RELATED INSTRUMENTS AND METHODS FOR USE IN IMPLANTING AN ARTIFICIAL INTERVERTEBRAL DISC

(75) Inventors: Joseph P. Errico, Green Brook, NJ (US); Michael W. Dudasik, Nutley, NJ (US); Rafail Zubok, Midland Park, NJ (US)

(73) Assignee: SpineCore, Inc., Summit, NJ (US)

( * ) Notice: Subject to any disclaimer, the term of this patent is extended or adjusted under 35 U.S.C. 154(b) by 598 days.

(21) Appl. No.: 10/309,585

(22) Filed: Dec. 4, 2002

(65) Prior Publication Data

US 2003/0078590 A1 Apr. 24, 2003

Related U.S. Application Data

(63) Continuation-in-part of application No. 10/282,356, filed on Oct. 29, 2002, which is a continuation-in-part of application No. 10/256,160, filed on Sep. 26, 2002, which is a continuation-in-part of application No. 10/175,417, filed on Jun. 19, 2002, which is a continuation-in-part of application No. 10/151,280, filed on May 20, 2002, which is a continuation-in-part of application No. 09/970,479, filed on Oct. 4, 2001, now Pat. No. 6,669,730, said application No. 10/309,585, is a continuation-in-part of application No. 10/140,153, filed on May 7, 2002, and a continuation-in-part of application No. 09/968,046, filed on Oct. 1, 2001, now abandoned, and a continuation-in-part of application No. 09/970,479, filed on Oct. 4, 2001, now Pat. No. 6,669,730, and a continuation-in-part of application No. 10/128,619, filed on Apr. 23, 2002, now Pat. No. 6,863,689, which is a continuation-in-part of application No. 09/906,119, filed on Jul. 16, 2001, now Pat. No. 6,607,559, said application No. 10/309,585, is a continuation-in-part of application No. 09/982,148, filed on Oct. 18, 2001, now Pat. No. 6,673,113.

(51) Int. Cl.
*A61B 17/56* (2006.01)

(52) U.S. Cl. .......................................... 606/86; 606/61

(58) Field of Classification Search .................. 606/86, 606/90, 105, 99, 61; 623/17.11–17.16

See application file for complete search history.

(56) References Cited

U.S. PATENT DOCUMENTS

| | | | |
|---|---|---|---|
| 3,867,728 A | 2/1975 | Stubstad et al. | |
| 4,309,777 A | 1/1982 | Patil | |
| 4,605,417 A | 8/1986 | Fleischauer | |
| 4,759,769 A | 7/1988 | Hedman et al. | |
| 4,932,969 A | 6/1990 | Frey et al. | |
| 4,997,432 A | 3/1991 | Keller | |
| 5,236,460 A | 8/1993 | Barber | |
| 5,314,477 A | 5/1994 | Marnay | |
| 5,370,697 A | 12/1994 | Baumgartner | |
| 5,401,269 A | 3/1995 | Buttner-Janz et al. | |
| 5,425,773 A | 6/1995 | Boyd et al. | |
| 5,507,816 A | 4/1996 | Bullivant | |
| 5,556,431 A | 9/1996 | Buttner-Janz | |
| 5,562,738 A | 10/1996 | Boyd et al. | |
| 5,676,701 A | 10/1997 | Yuan et al. | |
| 5,683,464 A | * 11/1997 | Wagner et al. ........... | 623/17.16 |
| 5,683,465 A | 11/1997 | Shinn et al. | |
| 5,782,830 A | 7/1998 | Farris | |
| 5,782,832 A | 7/1998 | Larsen et al. | |

(Continued)

*Primary Examiner*—Glenn K. Dawson
*Assistant Examiner*—D. Jacob Davis
(74) *Attorney, Agent, or Firm*—Lerner, David, Littenberg, Krumholz & Mentlik, LLP

(57) ABSTRACT

Instrumentation for distracting an intervertebral space and determining an appropriate size for an artificial intervertebral disc to be implanted therein include static trials and a static trial holder for manipulating the static trials. Each static trial is provided with at least one notch that is engaged by the static trial holder when the static trial is being manipulated thereby, to limit or prevent rotation of the static trial about a longitudinal axis with respect to the static trial holder during the manipulation.

12 Claims, 6 Drawing Sheets

Fig. 3c

U.S. PATENT DOCUMENTS

| | | |
|---|---|---|
| 5,893,889 A | 4/1999 | Harrington |
| 5,895,428 A | 4/1999 | Berry |
| 5,899,941 A | 5/1999 | Nishijima et al. |
| 5,989,291 A | 11/1999 | Ralph et al. |
| 6,039,763 A | 3/2000 | Shelokov |
| 6,066,174 A * | 5/2000 | Farris .................... 606/206 |
| 6,113,639 A | 9/2000 | Ray et al. |
| 6,159,215 A | 12/2000 | Urbahns et al. |
| 6,174,311 B1 | 1/2001 | Branch et al. |
| 6,224,607 B1 | 5/2001 | Michelson |
| 6,280,458 B1 | 8/2001 | Boche et al. |
| 6,319,257 B1 | 11/2001 | Carignan et al. |
| 6,368,350 B1 | 4/2002 | Erickson et al. |
| 6,375,682 B1 | 4/2002 | Fleischmann et al. |
| 6,428,544 B1 | 8/2002 | Ralph et al. |
| 6,436,102 B1 | 8/2002 | Ralph et al. |
| 6,471,725 B1 | 10/2002 | Ralph et al. |
| 6,478,800 B1 | 11/2002 | Fraser et al. |
| 6,517,580 B1 | 2/2003 | Ramadan et al. |
| 6,554,864 B1 | 4/2003 | Ralph et al. |
| 6,582,466 B1 | 6/2003 | Gauchet |
| 6,610,092 B1 | 8/2003 | Ralph et al. |
| 6,645,249 B1 | 11/2003 | Ralph et al. |
| 6,652,233 B1 | 11/2003 | Otake |
| 6,669,699 B1 | 12/2003 | Ralph et al. |
| 6,673,113 B1 | 1/2004 | Ralph et al. |
| 6,682,562 B1 | 1/2004 | Viart et al. |
| 6,706,068 B1 | 3/2004 | Ferree |
| 2001/0012938 A1 | 8/2001 | Zuckerman et al. |
| 2001/0016773 A1 | 8/2001 | Serhan et al. |
| 2001/0020170 A1 | 9/2001 | Zucherman et al. |
| 2002/0111681 A1 | 8/2002 | Ralph et al. |
| 2003/0014110 A1 | 1/2003 | Ralph et al. |
| 2003/0014112 A1 | 1/2003 | Ralph et al. |
| 2003/0028249 A1 | 2/2003 | Baccelli et al. |
| 2003/0055503 A1 | 3/2003 | O'Neil |
| 2003/0060886 A1 | 3/2003 | Van Hoeck et al. |
| 2003/0069586 A1 | 4/2003 | Errico et al. |
| 2003/0069642 A1 | 4/2003 | Ralph et al. |
| 2003/0074067 A1 | 4/2003 | Errico et al. |
| 2003/0149438 A1 * | 8/2003 | Nichols et al. ................ 606/99 |
| 2003/0149482 A1 | 8/2003 | Michelson |
| 2003/0204260 A1 | 10/2003 | Ferree |
| 2003/0208271 A1 | 11/2003 | Kuras |
| 2003/0216744 A1 | 11/2003 | Longhini et al. |
| 2003/0233097 A1 | 12/2003 | Ferree |
| 2003/0233148 A1 | 12/2003 | Ferree |
| 2004/0002759 A1 | 1/2004 | Ferree |
| 2004/0002762 A1 | 1/2004 | Hawkins |
| 2004/0010316 A1 | 1/2004 | William et al. |
| 2004/0030387 A1 * | 2/2004 | Landry et al. ........... 623/16.11 |
| 2004/0030389 A1 | 2/2004 | Ferree |
| 2004/0030390 A1 | 2/2004 | Ferree |
| 2004/0034426 A1 | 2/2004 | Errico et al. |
| 2004/0078079 A1 * | 4/2004 | Foley ...................... 623/17.11 |

* cited by examiner (Section A-A of Fig. 1a)

(Section B-B of Fig. 1a)

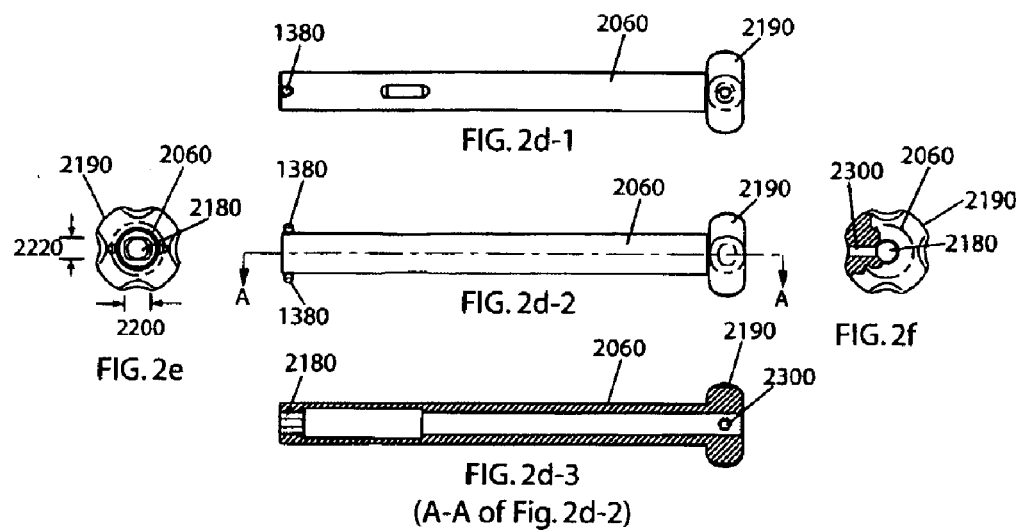
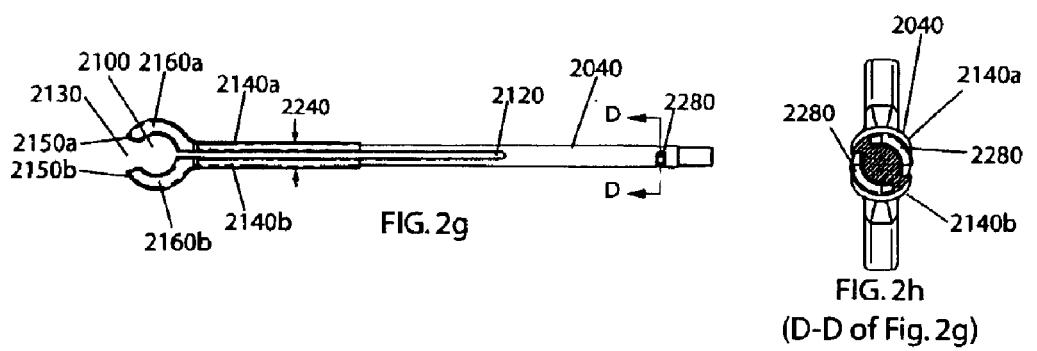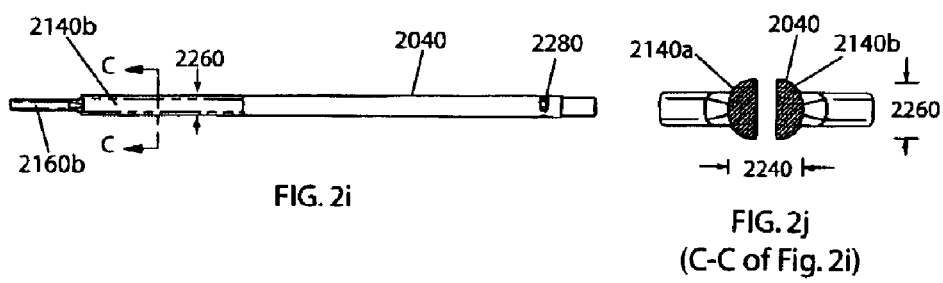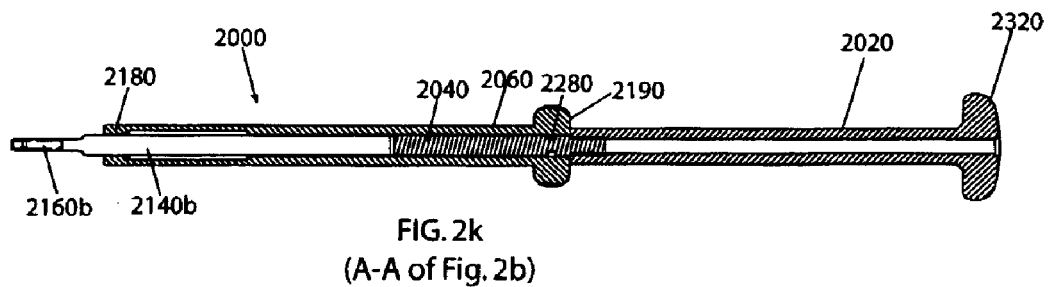

STATIC TRIALS AND RELATED INSTRUMENTS AND METHODS FOR USE IN IMPLANTING AN ARTIFICIAL INTERVERTEBRAL DISC

CROSS-REFERENCE TO RELATED APPLICATIONS

The present application is a continuation-in-part of U.S. patent application Ser. No. 10/282,356 (filed Oct. 29, 2002) entitled "Instrumentation and Methods For Use In Implanting an Artificial Intervertebral Disc", which is a continuation-in-Part of U.S. patent application Ser. No. 10/256,160 (filed Sep. 26, 2002) entitled "Artificial Intervertebral Disc Having Limited Rotation Using a Captured Ball and Socket Joint With a Solid Ball and Compression Locking Post", which is a continuation-in-part of U.S. patent application Ser. No. 10/175,417 (filed Jun. 19, 2002) entitled "Artificial Intervertebral Disc Utilizing a Ball Joint Coupling", which is a continuation-in-part of U.S. patent application Ser. No. 10/151,280 (filed May 20, 2002) entitled "Tension Bearing Artificial Disc providing a Centroid of Motion Centrally Located Within an Intervertebral Space", which is a continuation-in-part of both U.S. patent application Ser. No. 09/970,479 (filed Oct. 4, 2001) entitled "Intervertebral Spacer Device Utilizing a Spirally Slotted Belleville Washer Having Radially Extending Grooves", now U.S. Pat. No. 6,669,730 as well as U.S. patent application Ser. No. 10/140,153 (filed May 7, 2002) entitled "Artificial Intervertebral Disc Having a Flexible Wire Mesh Vertebral Body Contact Element", the former being a continuation-in-part of U.S. patent application Ser. No. 09/968,046 (filed Oct. 1, 2001) entitled "Intervertebral Spacer Device Utilizing a Belleville Washer Having Radially Extending Grooves", now abandoned and the latter being a continuation-in-part of both U.S. patent application Ser. No. 09/970,479 (detailed above) as well as U.S. patent application Ser. No. 10/128,619 (filed Apr. 23, 2002) entitled "Intervertebral Spacer Having a Flexible Wire Mesh Vertebral Body Contact Element", now U.S. Pat. No. 6,863,689 which is a continuation-in-part of both U.S. patent application Ser. No. 09/906,119 (filed Jul. 16, 2001) and entitled "Trial Intervertebral Distraction Spacers", now U.S. Pat. No. 6,607,559, as well as U.S. patent application Ser. No. 09/982,148 (filed Oct. 18, 2001) and entitled "Intervertebral Spacer Device Having Arch Shaped Spring Elements", now U.S. Pat. No. 6,673,113. All of the above mentioned applications are hereby incorporated by reference herein in their respective entireties.

FIELD OF THE INVENTION

This invention relates generally to systems and methods for use in spine arthroplasty, and more specifically to instruments for distracting an intervertebral space and for inserting and removing trial artificial intervertebral discs, and methods of use thereof.

BACKGROUND OF THE INVENTION

The bones and connective tissue of an adult human spinal column consists of more than twenty discrete bones coupled sequentially to one another by a tri-joint complex that consists of an anterior disc and the two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. With respect to the failure of the intervertebral disc, and the insertion of implants and/or height restorative devices, several methods and devices have been disclosed in the prior art that achieve immobilization and/or fusion of adjacent bones by implanting artificial assemblies in or on the spinal column. More recently, the development of non-fusion implant devices, which purport to permit continued natural movement in the tri-joint complex, have provided great promise as a preferably alternative to fusion devices. The region of the back that needs to be corrected, as well as the individual variations in anatomy, determine the appropriate surgical protocol and implantation assembly. Generally, the preparation of the intervertebral space for the receipt of fusion or non-fusion devices involves removing the damaged disc material and thereafter distracting the adjacent vertebral bones to their appropriate distance apart. Once the proper height of the intervertebral space is restored, the fusion or non-fusion device can be implanted.

It is an object of the invention to provide instrumentation and methods that enable surgeons to more accurately, easily, and efficiently prepare the intervertebral space and implant fusion or non-fusion devices. Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which includes, among other aspects, static trial artificial intervertebral discs (sometimes referred to herein as a "static trial") and a static trial artificial intervertebral disc holder (sometimes referred to herein as a "static trial holder").

More particularly, the systems and methods disclosed herein are intended for use in spine arthroplasty procedures, and specifically for use with the systems and methods described herein in conjunction with the systems and methods in conjunction with the systems and methods described in U.S. patent application Ser. No. 10/282,356 (filed Oct. 29, 2002) entitled "Instrumentation and Methods For Use In Implanting an Artificial Intervertebral Disc" (hereinafter referred to as "the '356 application") as well as U.S. patent application Ser. No. 10/256,160 (filed Sep. 26, 2002)

entitled "Artificial Intervertebral Disc Having Limited Rotation Using a Captured Ball and Socket Joint With a Solid Ball and Compression Locking Post" (hereinafter referred to as "the '160 application") as well as U.S. patent application Ser. No. 09/906,127 (filed Jul. 16, 2001) entitled "Insertion Tool For Use With Intervertebral Spacers" (hereinafter referred to as "the '127 application"), both applications of which are mentioned above. However, it should be understood that the systems and methods described herein are also suitable for use with other systems and methods without departing from the scope of the invention.

For example, while the static trials described herein are primarily intended for use in determining the appropriate size of particular embodiments of the artificial intervertebral disc implants described in the '356 and '160 applications to be implanted (or whether a particular size can be implanted) into the distracted intervertebral space, they can also be used for determining the appropriate size of any other suitably configured orthopedic implant or trial to be implanted (or whether a particular size can be implanted) into the distracted intervertebral space. Further, they can also be used as static stabilization devices for use in, for example, fusion procedures, in that the surgeon can leave one of the static trials implanted in the intervertebral space to facilitate fusion. Preferred embodiments for such use include static trials having an osteoinductive or osteoconductive surface, such as, for example, a porous surface.

And, for example, while the static trial holder described herein is primarily intended for use in holding, inserting, removing, and otherwise manipulating the static trials described herein in a manner that limits or prevents movement of the static trial relative to the static trial holder, it can also be used for manipulating any embodiment of the trial spacers described in the '127 application (also referred to therein and herein as distraction spacers), and can also be used for manipulating any other suitably configured orthopedic device, provided the same has been modified to have features (such as, for example, those describe herein on the static trials described herein) that are engageable by the static trial holder to limit or prevent movement of the device relative to the static trial holder.

While the instrumentation described herein (e.g., the static trials and static trial holder) will be discussed for use with the artificial intervertebral disc of FIGS. 1g–n of the '356 application, such discussions are merely by way of example and not intended to be limiting of their uses. Thus, it should be understood that the instrumentation and methods can be used with any of the artificial intervertebral discs disclosed in the '356 or '160 applications, or any other artificial intervertebral disc having (or being modifiable or modified to have) suitable features therefor. Moreover, it is anticipated that the features of the static trials (e.g., cylindrical trunks and engagement notches) that are used by the static trial holder discussed herein to hold and/or manipulate the static trials can be applied, individually or collectively or in various combinations, to other trials, spacers, artificial intervertebral discs or other orthopedic devices as standalone innovative features for enabling such trials, spacers, artificial intervertebral discs, or other orthopedic devices to be more efficiently and more effectively held and/or manipulated by the static trial holder described herein or by other tools having suitable features. In addition, it should be understood that the invention encompasses artificial intervertebral discs, spacers, trials (static or dynamic), and/or other orthopedic devices, that have one or more of the features disclosed herein, in any combination, and that the invention is therefore not limited to artificial intervertebral discs, spacers, trials, and/or other orthopedic devices having all of the features simultaneously.

More particularly with regard to the static trials described herein, a plurality of static trials are provided primarily for use in determining the appropriate size of an artificial intervertebral disc to be implanted (or whether a particular size of the artificial intervertebral disc can be implanted) into the distracted intervertebral space (e.g., the artificial intervertebral disc 160 of FIGS. 1g–n of the '356 application). Preferably, for each artificial intervertebral disc to be implanted, a plurality of sizes of the artificial intervertebral disc would be available. That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs. Accordingly, preferably, each of the plurality of static trials for use with a particular plurality of differently sized artificial intervertebral discs would have a respective width and depth dimension set corresponding to the width and depth of a respective one of the plurality of differently sized artificial intervertebral discs. For example, the plurality of static trials for use with the set of artificial intervertebral discs described for example could include static trials having widths being either 35 mm or 40 mm, and depths ranging from 14 mm to 18 mm in 1 mm increments, for a total of 10 static trials. It should be understood that the artificial intervertebral discs and/or the static trials can be offered in a variety of dimensions without departing from the scope of the invention, and that the dimensions specifically identified and quantified herein are merely exemplary. Moreover, it should be understood that the set of static trials need not include the same number of trials for each artificial intervertebral disc in the set of artificial intervertebral discs, but rather, none, one, or more than one trial can be included in the trial set for any particular artificial intervertebral disc in the set.

Each of the plurality of static trials preferably further includes features that can be used by the static trial holder (described below), the inserter/impactor described in the '356 application, and the repositioners/extractors described in the '356 application. With regard to a feature that can be used by the static trial holder, each static trial preferably includes a recess that can be gripped by the opposing semicircular extents of the static trial holder. Preferably, this recess forms a perimetrical groove (a groove that extends around at least a portion of the perimeter of the static trial, e.g., an annular groove) that establishes a trunk (e.g., a cylindrical trunk) between the baseplates of the static trial, such that the baseplates extend as flanges from either end of the trunk. Accordingly, preferably, the opposing semicircular extents each have a thickness smaller than the width of the annular groove, and as such fit into the annular groove to grip the cylindrical trunk between them.

Additional features that can be used by the static trial holder include (on any static trial surface that faces the desired engagement approach direction of the static trial holder, e.g., on each of the anteriorly facing and anterior-laterally facing flat surfaces of the static trial as described below) opposing recesses, preferably formed as upper and lower notches, an upper notch in the upper baseplates and a lower notch in the lower baseplate. Preferably, the notches are sized so that the opposing notches of each pair form a volume that is dimensioned to closely accommodate the dimensions of the static trial holder's prongs' cross-section. That is, as described below, the body of each prong is thicker than the semicircular extent that extends from the body, and as such, whereas the semicircular extents fit into the annular groove, the prongs do not because their thickness is greater than the width of the annular groove opening. Each notch pair accommodates this greater thickness, and as such, as the opposing semicircular extents of the static trial holder are placed into the annular groove, the bodies of the prongs of the static trial holder pass into the notches so that the semicircular extents can continue into the annular groove and be seated around the cylindrical trunk. Once the prongs are fitted within the notch pair, interference between the prongs and the notch walls limits or prevents rotation of the static trial about a longitudinal axis (e.g., an axis parallel to the longitudinal axis of the cylindrical trunk) with respect to the static trial holder.

With regard to features that can be used by the inserter/impactor described in the '356 application, each static trial (and each artificial intervertebral disc that the trials approximate) preferably includes an anteriorly facing flat surface, flanked by two anteriolaterally facing flat surfaces (one on each side of the anteriorly facing flat surface), and, to provide for holding of the static trial or disc for an anterior insertion approach, a hole spaced from the anteriorly facing flat surface, the hole having a longitudinal axis parallel to the anteriorly facing flat surface. The holding pin of the inserter/impactor fits within the hole, and the angled flat surfaces of the static trial or disc fit against the correspondingly angled flat surfaces of the inserter/impactor, and operation of the inserter/impactor pulls the holding pin toward the flat surface of the inserter/impactor opposite the pin, to rigidly hold the static trial or disc by the baseplate. When the static trial is held in this manner, rotation of the static trial or disc about a longitudinal axis (e.g., in the case of the trials, an axis parallel to the longitudinal axis of the cylindrical trunk) relative to the inserter/impactor is prevented by interference of the corners of the static trial's or disc's flat surfaces and the corners of the inserter/impactor's flat surfaces, similar to the manner in which a wrench holding a nut prevents rotation of the nut relative to the wrench. Further, the holding of the static trial or disc in this manner allows for some repositioning of the static trial or disc in the intervertebral space via rotation of the static trial or disc in either direction about the longitudinal axis of the intervertebral space.

Preferably, both of the baseplates of the static trial or disc have similarly configured flat surfaces, and both baseplates' flat surfaces fit against the angled flat surfaces of the inserter/impactor to provide for a more secure holding of the static trial or disc by the inserter/impactor. Also preferably, in order to provide for a holding of the static trial or disc for two additional (here, anteriolateral) insertion approaches, each static trial or disc also includes two additional holes, one spaced apart from one of the anteriolaterally facing flat surfaces, and the other spaced apart from the other of the anteriolaterally facing flat surfaces. Accordingly, operation of the inserter/impactor can fit the holding pin into either of these two additional holes, and hold the anteriolaterally facing flat surface (the one associated with the hole into which the pin is fit) of the static trial or disc against the flat surface of the inserter/impactor opposite the pin. It should be understood that preferably, in order to facilitate these two additional approaches, the angle separating the anteriorly facing flat surface of the static trial or disc and one of the anteriolaterally facing flat surfaces of the static trial or disc is equal to the angle separating the anteriorly facing flat surface and the other of the anteriolaterally facing flat surfaces.

With regard to features that can be used by the repositioners/extractors described in the '356 application, each static trial (and each artificial intervertebral disc that the trials approximate) preferably includes at least two holes extending longitudinally into one of the baseplates of the trial or disc from the inwardly facing surface of the baseplate. More than two holes can be used to provide for multiple repositioning/extracting approaches. Preferably, in order for the same repositioning/extracting tool to be used for multiple approaches on the same trial or artificial intervertebral disc, adjacent holes should be separated by the same distance separating other adjacent holes.

As discussed in greater detail in the '356 application with regard to the repositioners/extractors, in order to engage two of the holes, each repositioner/extractor has two pins extending in parallel from a central shaft, perpendicular to the longitudinal axis of the central shaft. The pins can be inserted into the holes, and pulling or pushing on the central shaft along its longitudinal axis when the holes are engaged pulls or pushes the static trial or artificial intervertebral disc in the intervertebral space. Further, because two holes are engaged, the static trial or artificial intervertebral disc can be rotated in either direction about a longitudinal axis passing through the intervertebral space, by rotating of the central shaft of the repositioner/extractor about its distal end, about an axis parallel to the longitudinal axes of the pins.

On each repositioner/extractor, the pins are formed on prongs that extend laterally from the central shaft. The direction of the prongs, and the location of the pins relative to the central shaft, determine the angle or angles of surgical approach for which a particular repositioner/extractor can be used. Further, the number and location of holes further determine the angle or angles of surgical approach for which a particular repositioner/extractor can be used. Accordingly, the present invention contemplates a variety of repositioner/extractors, and a variety of holes configurations, to provide the surgeon with a variety of possible surgical approach angles.

For example, three repositioner/extractors (symmetric, offset left, and offset right) and two hole configurations are illustrated and described in greater detail in the '356 application. A first hole configuration includes the hole configuration described above, that is, three holes on one of the baseplates, the holes being configured so that a first hole is located in the anterior-posterior plane, and the adjacent (second and third) holes are located in respective opposing anteriolateral planes on either side of the first hole. This first hole configuration is described for and illustrated on both of the baseplates of the static trial of the present invention. A second hole configuration (described in the '356 application but not illustrated herein) includes four holes on one of the baseplates (e.g., the upper baseplate), the holes being configured so that first and second holes straddle the anterior-posterior plane, a third hole is located so that the third hole and the first hole straddle one of the opposing anteriolateral planes, and a fourth hole is located so that the fourth hole and the second hole straddle the other of the opposing anteriolateral planes.

With further regard to the static trial holder described herein, the static trial holder is provided primarily for use in holding, inserting, removing, and otherwise manipulating the static trials described herein. Preferably, as briefly mentioned above, the static trial holder has at an end of an extension of the static trial holder a pair of opposing prongs that open away from one another and close toward one another. Each of the prongs has a semicircular extent and the semicircular extents face one another to define a circular holding enclosure that is useful for capturing the cylindrical trunk of the static trial between them. The prongs are spring biased toward a neutral position such that the holding enclosure is spring biased to a receptive state in which the cylindrical trunk can be snapped into (or out of) the holding enclosure by temporarily placing the holding enclosure in an expanded state (by forcing the cylindrical trunk against the mouth of the enclosure) that allows passage of the cylindrical trunk through the mouth of the enclosure. Once the cylindrical trunk is in the enclosure, the holding enclosure can be placed in a contracted state, or locked, where the trial is more securely held, so that the trial will not escape the holding enclosure as it is experiencing greater forces while being inserted and removed from the intervertebral space. This locking is effected by rotating a sleeve that surrounds the prongs. The bore of the sleeve is configured to press the prongs together when the sleeve is rotated a quarter turn (ninety degrees), and to allow them to separate when the sleeve is reverse rotated a quarter turn (in some embodiments, either quarter turn is in either direction; in the embodiments illustrated herein, the quarter turn that separates the prongs is a reverse rotation of the quarter turn that presses them together). The sleeve stops its rotation at either the "locked" or "unlocked" states of the holding enclosure, due to radially inwardly directed screw heads on the sleeve's inner surface that ride in ninety-degree arc grooves on the extension's outer surface and that stop when the end of the groove is reached.

Further, as discussed above, each static trial includes (on any static trial surface that faces the desired engagement approach direction of the static trial holder, e.g., on each of the anteriorly facing and anterior-laterally facing flat surfaces of the static trial as described below) opposing recesses, preferably formed as upper and lower notches, an upper notch in the upper baseplates and a lower notch in the lower baseplate. Preferably, the notches are sized so that the opposing notches of each pair form a volume that is dimensioned to closely accommodate the dimensions of the static trial holder's prongs' cross-section. That is, as described below, the body of each prong is thicker than the semicircular extent that extends from the body, and as such, whereas the semicircular extents fit into the annular groove, the prongs do not because their thickness is greater than the width of the annular groove opening. Each notch pair accommodates this greater thickness, and as such, as the opposing semicircular extents of the static trial holder are placed into the annular groove, the bodies of the prongs of the static trial holder pass into the notches so that the semicircular extents can continue into the annular groove and be seated around the cylindrical trunk. Once the prongs are fitted within the notch pair, interference between the prongs and the notch walls limits or prevents rotation of the static trial about a longitudinal axis (e.g., an axis parallel to the longitudinal axis of the cylindrical trunk) with respect to the static trial holder.

It should be understood that when the static trial is being held (either when the holding enclosure is in its receptive state or in its contracted state), because the semicylindrical extents fit within the annular groove of the static trial, the static trial will not escape from the enclosure along the longitudinal axis of the cylindrical trunk. While the static trial holder is discussed herein as primarily used for manipulating the static trials, it is preferably is also useful for manipulating the distraction spacers described in the '127 application, in that the semicircular extents of the pincers preferably also interact with the annular grooves and cylindrical trunks of those distraction spacers in the same manner as described herein.

Further, the sleeve preferably has on its exterior surface at least one stop protrusion that is positioned and dimensioned to extend dorsally or ventrally from the exterior surface when the holding enclosure is in its "locked" state, so that when the surgeon inserts the static trial into the intervertebral space, the stop protrusions prevent the static trial from being inserted too far into the space (that is, so that the stop protrusions hit against the lips of the adjacent vertebral body endplates before the static trial is inserted too far).

BRIEF DESCRIPTION OF THE DRAWINGS

FIGS. 2a–k show side (FIG. 2a), top (FIG. 2b), perspective (FIG. 2c), disassembly (FIG. 2d1, 2d2, 2d3, and 2e–j), and side cutaway (FIG. 2k) views of a static trial holder of the present invention.

FIGS. 3d–e show top views of the static trial holder of FIGS. 2a–k holding a static trial of FIGS. 1a–f from two anterior-lateral approach holds.

DETAILED DESCRIPTION OF THE PREFERRED EMBODIMENTS

Figure 1A:
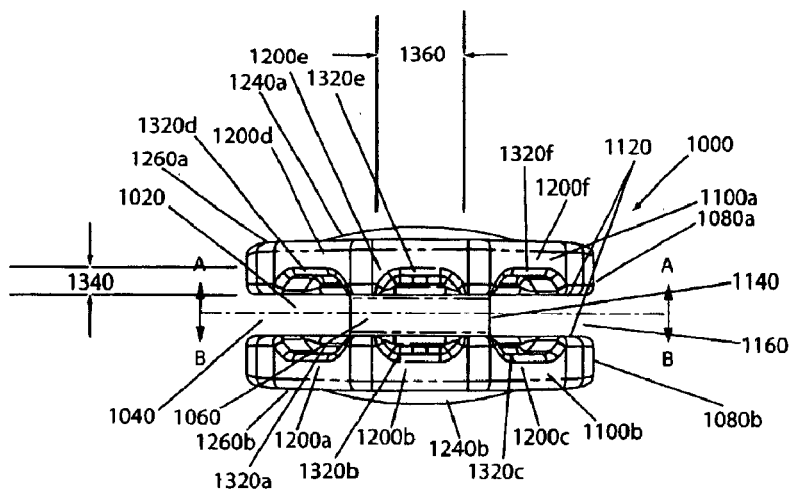
FIGS. 1a–f show front (FIG. 1a), side (FIG. 1b), perspective (FIG. 1c), top (FIG. 1d), bottom cutaway (FIG. 1e) and top cutaway (FIG. 1f) views of a static trial of the present invention.
Figure 1B:
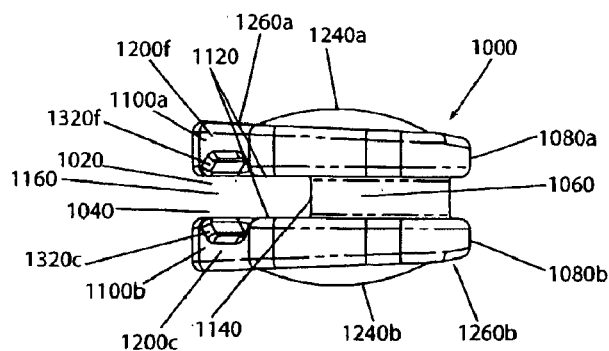
Figure 1C:
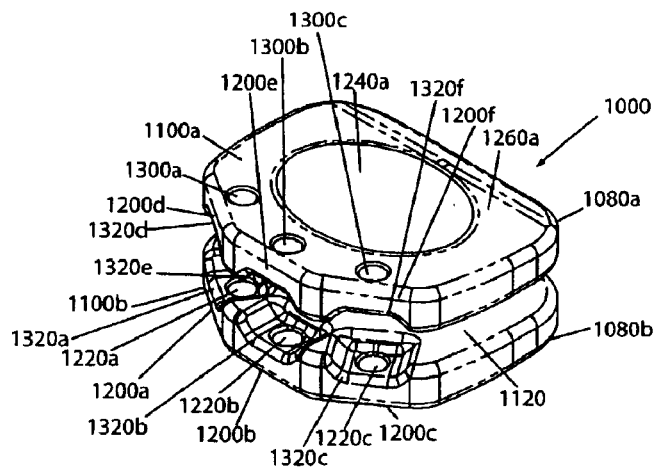
Figure 1D:
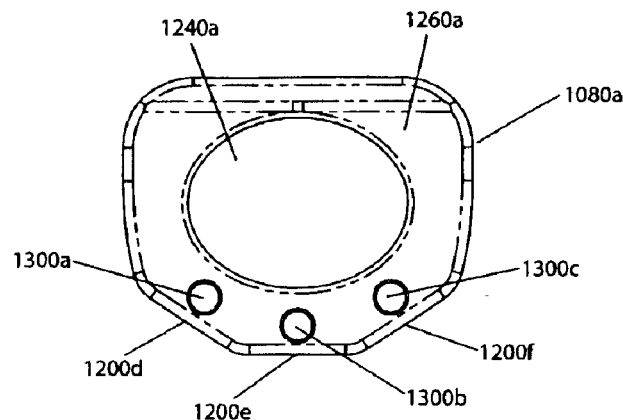
Figure 1E:
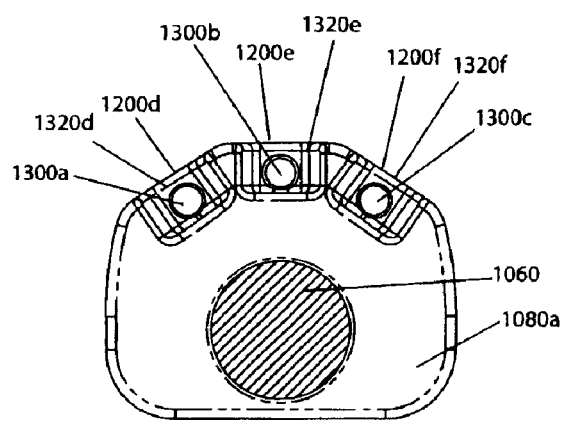
Figure 1F:
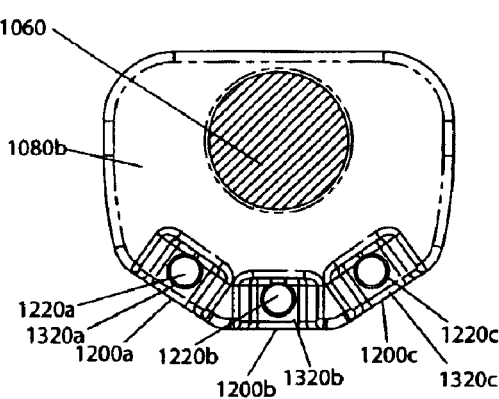
Figure 2A:
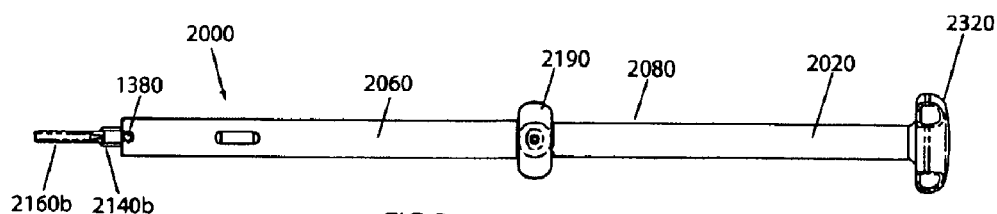
Figure 2B:
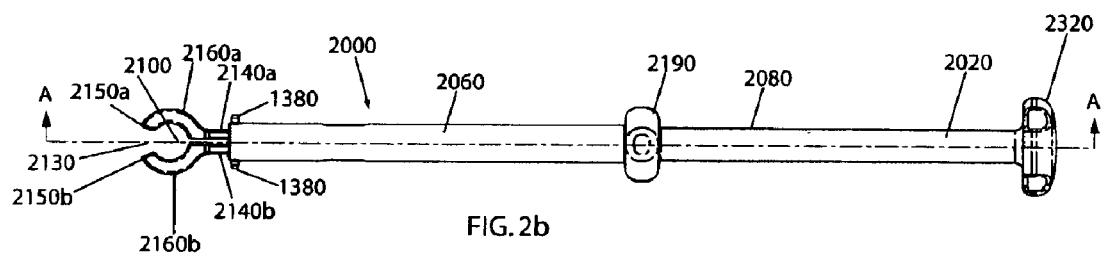
Figure 2C:
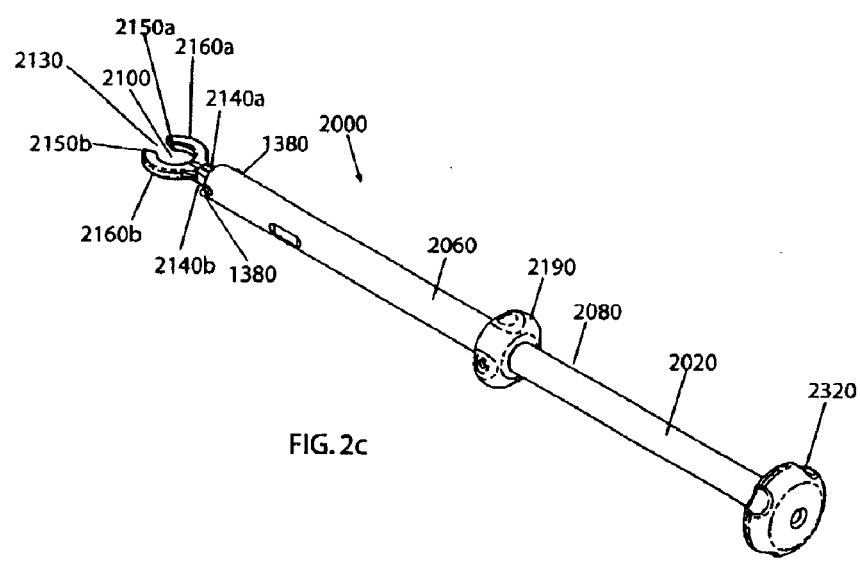

While the invention will be described more fully hereinafter with reference to the accompanying drawings, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

A preferred embodiment of a static trial of the present invention, for use with the static trial holder of the present invention, will now be described.

Referring now to FIGS. 1a–f, a static trial of the present invention is shown in front (FIG. 1a), side (FIG. 1b), perspective (FIG. 1c), top (FIG. 1d), bottom cutaway (FIG. 1e) and top cutaway (FIG. 1f) views.

It should be understood that the illustration and reference herein to the artificial intervertebral disc shown in FIGS. 1g–n of the '356 application is merely to show an example of one type of artificial intervertebral disc that is contemplated by, encompassed by, and suitable for use with, the present invention, and that such illustration and reference herein is not meant to limit the scope of the present invention or limit the uses of the present invention. Rather, any other artificial intervertebral disc (or any other orthopedic device) having suitable features for being used with the instrumentation and methods described herein are contemplated by the present invention. Indeed, the features suitable for manipulation (e.g., angled flat surfaces with adjacent holes and/or opposing notches) are encompassed by the present invention, regardless of to what orthopedic device they may be applied. Other exemplary suitable artificial intervertebral discs include, but are not limited to, the artificial intervertebral discs described in the '160 application with regard to FIGS. 8*a–y*, 9*a–t*, 10*a–t*, 11*a–j*, and 12*a–o* thereof and by the accompanying descriptions therefor (e.g., embodiments identified as the first, second, third, fourth, and fifth preferred embodiments of the fourth embodiment family, etc.). It should be noted that, as can be seen from FIGS. 1*g–n* of the '356 application, that the artificial intervertebral disc shown in FIGS. 1*g–n* of the '356 application has features similar to those of these other suitable artificial intervertebral discs of the '160 application, and it should be understood that such similar features are structurally and functionally as described in the '160 application. Such similar features include an inwardly facing surface of the upper baseplate, and a convex structure on the lower baseplate, the convex structure having an inwardly facing surface.

And, while the instrumentation described herein (e.g., the static trials and static trial holder) as well as the instrumentation described in the '356 application (e.g., the static trials, static trial holder, dynamic trial, inserter/impactor, repositioners/extractors, and leveler described therein) will be discussed for use with the artificial intervertebral disc of FIGS. 1*g–n* of the '356 application, such discussions are merely by way of example and not intended to be limiting of their uses. Thus, it should be understood that the tools can be used with any of the artificial intervertebral discs disclosed in the '356 application or the '160 application, or any other artificial intervertebral disc having (or being modifiable or modified to have) suitable features therefor. Moreover, it is anticipated that the features of the artificial intervertebral disc (e.g., the flat surfaces and accompanying holes) and/or the static trials (e.g., the cylindrical trunks and flat surfaces and accompanying holes and/or engagement notches) that are used by the tools discussed herein (or in the '356 application) to hold and/or manipulate these devices (certain features, it should be noted, were first shown and disclosed in the '160 application, the '127 application, and/or the '356 application) can be applied, individually or collectively or in various combinations, to other trials, spacers, artificial intervertebral discs or other orthopedic devices as stand-alone innovative features for enabling such trials, spacers, artificial intervertebral discs, or other orthopedic devices to be more efficiently and more effectively held and/or manipulated by the tools described herein (or in the '356 application) or by other tools having suitable features. In addition, it should be understood that the invention encompasses artificial intervertebral discs, spacers, trials (static or dynamic), and/or other orthopedic devices, that have one or more of the features disclosed herein (or in the '356 application), in any combination, and that the invention is therefore not limited to artificial intervertebral discs, spacers, trials, and/or other orthopedic devices having all of the features simultaneously.

A plurality of static trials 1000 are provided primarily for use in determining the appropriate size of an artificial intervertebral disc to be implanted (or whether a particular size of the artificial intervertebral disc can be implanted) into the distracted intervertebral space (e.g., the artificial intervertebral disc 160 of FIGS. 1*g–n* of the '356 application). Preferably, for each artificial intervertebral disc to be implanted, a plurality of sizes of the artificial intervertebral disc would be available. That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs. Accordingly, preferably, each of the plurality of static trials 1000 for use with a particular plurality of differently sized artificial intervertebral discs would have a respective width and depth dimension set corresponding to the width and depth of a respective one of the plurality of differently sized artificial intervertebral discs. For example, the plurality of static trials 1000 for use with the set of artificial intervertebral discs described for example could include static trials 1000 having widths being either 35 mm or 40 mm, and depths ranging from 14 mm to 18 mm in 1 mm increments, for a total of 10 static trials. It should be understood that the artificial intervertebral discs and/or the static trials 1000 can be offered in a variety of dimensions without departing from the scope of the invention, and that the dimensions specifically identified and quantified herein are merely exemplary. Moreover, it should be understood that the set of static trials 1000 need not include the same number of trials for each artificial intervertebral disc in the set of artificial intervertebral discs, but rather, none, one, or more than one trial can be included in the trial set for any particular artificial intervertebral disc in the set.

Each of the static trials (the static trial 1000 shown is exemplary for all of the static trials in the plurality of static trials; preferably the static trials in the plurality differ from one another only with regard to overall dimensions as described above) includes at least one feature that can be engaged by a tool. Suitable tools include, but are not limited to, the static trial holder 2000 described herein, the static trial holder 200 described in the '356 application, the inserter/impactor described in the '356 application, and the repositioners/extractors described in the '356 application. It should be understood that with respect to manipulating the static trials 1000 with the tools described in the '356 application, such manipulation is the same as the manipulation of the static trials 100 of the '356 application with such tools as described in the '356 application, with respect to the static trials 1000 and the static trials 100 having similar features for manipulation therefor and thereby (e.g., cylindrical trunks and flat surfaces and accompanying holes). It should be further understood that with respect to manipulating the static trials 100 with the static trial holder 2000 described herein, such manipulation is the same as the manipulation of the static trials 1000 of this application with such static trial holder 2000 as described herein, with respect to the static trials 100 and the static trials 1000 having similar features for manipulation therefor and thereby (e.g., cylindrical trunks).

Specifically, the static trial 1000 includes a recess 1020 that can be gripped by the opposing semicircular extents 2160*a–b* of the static trial holder 2000. Preferably, this recess 1020 forms an annular groove 1040 that establishes a cylindrical trunk 1060 between the upper and lower baseplates 1080*a–b* of the static trial 1000, such that the baseplates 1080*a–b* extend as flanges 1100*a–b* from either end of the cylindrical trunk 1060. Accordingly, preferably, the opposing semicircular extents 2160*a–b* each have a thickness smaller than the width of the annular groove 1040, and as such fit into the annular groove 1040 to grip the cylindrical trunk 1060 between them. (Importantly, as discussed in greater detail below, the body of the prongs 2140*a–b* (from which the semicircular extents 2160*a–b* extend) has a thickness greater than the width of the annular groove 1040 (and as such does not fit within the annular groove) but small enough to be accommodated by the opposing notches 1320*a–b* of the static trial 1000 as described below.)

In some embodiments, while not shown in FIGS. 1*a–f*, it is also preferable that the annular groove 1040 radially widen outwardly, such that the walls 1120 of the annular groove 1040 are tapered toward one another with the increasing depth of the groove 1040, such that the floor 1140 of the groove 1040 is more narrow than the opening 1160 of the groove 1040. Accordingly, preferably, in such embodiments, each semicircular extent 2160*a–b* correspondingly radially widens outwardly, such that the thinner portion of the extent 2160*a–b* fits closer to the floor 1140 of the annular groove 1040, so that the tapered surfaces of the extents 2160*a–b* compress against the tapered walls 1120 of the annular groove 1040 when the static trial 1000 is gripped by the static trial holder 2000. This taper locking provides for a secure grip so that the static trial 1000 can be manipulated accurately and efficiently.

In some embodiments, while not shown in FIGS. 1*a–f*, it is also preferable that the floor of the annular groove 1040 of the cylindrical trunk 1060 be ridged (e.g., have ridges that run parallel to the longitudinal axis of the cylindrical trunk), and the surfaces of the semicircular extents 2160*a–b* of the static trial holder 2000 that compress against the floor of the annular groove 1040 when the static trial holder 2000 grips the static trial 1000 be correspondingly provided with ridges. The interlocking of the ridges of the static trial 1000 with the ridges of the static trial holder 2000 when the static trial 1000 is gripped prevents rotation of the static trial 1000 about the longitudinal axis of the cylindrical trunk 1060 with respect to the static trial holder 2000.

Preferably, as shown in FIGS. 1*a–f*, each static trial 1000 includes (on any static trial surface that faces the desired engagement approach direction of the static trial holder 2000) opposing recesses, preferably formed as upper and lower notches, an upper notch in the upper baseplate and a lower notch in the lower baseplate. For example, opposing notches 1320*b* and 1320*e* are on each of the anteriorly facing flat surfaces of the upper 1080*a* and lower 1080*b* baseplates. And, for example, opposing notches 1320*a* and 1320*d* are on one of the anterior-laterally facing flat surfaces of the upper 1080*a* and lower 1080*b* baseplates. And, for example, opposing notches 1320*c* and 1320*f* are on the other of the anterior-laterally facing flat surfaces of the upper 1080*a* and lower 1080*b* baseplates. Preferably, the notches 1320*a–f* are sized so that the opposing notches of each pair (1320*a,d*, 1320*b,e*, and 1320*c,f*) form a volume that closely accommodates the dimensions of the static trial holder's 2000 prongs' 2140*a–b* cross-section. That is, as described below, the body of each prong 2140*a–b* is thicker than the semicircular extent 2160*a–b* that extends from the body, and as such, whereas the semicircular extents 2160*a–b* fit into the annular groove 1040, the prongs 2140*a–b* do not because the depth 2260 of their cross-section (described below) is greater than the width of the annular groove opening 1160. However, each notch pair (1320*a,d*, 1320*b,e*, and 1320*c,f*) accommodates this greater thickness, in that each notch 1320*a–f* has a depth 1340, and, when the two notch depths 1340 of the opposing notches of the notch pair are taken together with the width of the annular groove 1040, the combined distance accommodates the depth 2260 of the static trial holder's 2000 prongs' 2140*a–b* cross-section. Further, each notch 1320*a–f* has a width 1360 that accommodates the width 2240 of the static trial holder's 2000 prongs' 2140*a–b* cross-section. (It should be noted that the width 1360 accommodates the width 2240 of the static trial holder's 2000 prongs' 2140*a–b* cross-section even when the prongs 2140*a–b* are separated to place the holding enclosure 2100 in an expanded state as described below. This enables the notches 1320*a–f* to accommodate the width 2240 of the prongs' cross-section as the cylindrical trunk 1060 of the static trial 1000 is being snapped into the holding enclosure 2100 as described below.) As such, as the opposing semicircular extents 2160*a–b* of the static trial holder 2000 are placed into the annular groove 1040, the bodies of the prongs 2140*a–b* pass into the notches of the pair so that the semicircular extents 2160*a–b* can continue into the annular groove 1040 and be seated around the cylindrical trunk 1060. More specifically, the prongs 2140*a–b* of the static trial holder 2000 fit into the notches above and below it (e.g., 1320*b* and 1320*e* for an anterior approach; 1320*a* and 1320*d* for an anterior-lateral approach; and 1320*c* and 1320*f* for another anterior-lateral approach). Once the prongs 2140*a–b* are fitted within the notch pair, interference between the prongs 2140*a–b* and the notch walls limits or prevents rotation of the static trial 1000 about a longitudinal axis (e.g., an axis parallel to the longitudinal axis of the cylindrical trunk 1060) with respect to the static trial holder 2000.

It should be understood that configurations having more or fewer notches, and in a variety of locations, are contemplated by the invention, and the detailed descriptions of only one type of notch configuration is not meant to limit the invention to only this configuration. Importantly, the invention encompasses using a single notch in a baseplate, a single notch pair, or any number of notches or notch pairs, formed in any suitable manner with any suitable dimensions, in any number of locations on a spacer, a trial or an artificial intervertebral disc (not limited to locations on the baseplates), for purposes of enabling the spacer, trial, or disc to be engaged by a manipulation instrument (not limited to a static trial holder) that engages the notch, for the purpose of limiting rotation of the spacer, trial, or disc (or other orthopedic implant) with respect to the instrument or for any other purpose, and/or to enable the surgeon to work from a variety of approaches. For example, the notch configuration described herein, in cooperation with the static trial holder, provides the surgeon with the ability to work from a directly anterior approach, as well as two anteriolateral approaches. It should be understood that additional notch configurations can enable the surgeon to work from a directly posterior approach, posteriolateral approaches, directly lateral approaches, or anteriolateral approaches that are different than those illustrated. For example, the placement of one or more suitably spaced notches (or the addition of one or more notches) on the posterior edge, and/or one or both of the lateral edges of one or both of the baseplates, would enable the surgeon to use the static trial holder of the present invention to achieve such approaches.

Additionally with regard to features that can be engaged by a tool, each of the static trials 1000 includes at least one feature that can be engaged by a tool that preferably is also used to engage the artificial intervertebral disc that the trial approximates. Suitable tools that can grip both the trial and the artificial intervertebral disc include, but are not limited to, the inserter/impactor described in the '356 application. Specifically, for being engaged by the inserter/impactor, each static trial 1000 (and artificial intervertebral disc) includes an anteriorly facing flat surface 1200*b*, flanked by two anteriolaterally facing flat surfaces 1200*a* and 1200*c* (one on each side of the anteriorly facing flat surface 1200*b*), and, to provide for holding of the static trial 1000 (or disc) for an anterior insertion approach, a hole 1220*b* spaced from the anteriorly facing flat surface, the hole 1220*b* having a longitudinal axis parallel to the anteriorly facing flat surface 1200*b*.

As can be understood by the detailed description in the '356 application of the holding of the static trials 100 described therein (because the static trials 100 have a flat surface and hole configuration identical to that of the static trials 1000 described herein) by the inserter/impactor described therein, the holding pin of the inserter/impactor described in the '356 application fits within the hole 1220*b*, and the angled flat surfaces 1200*a–c* of the static trial 1000 (or disc) fit against the correspondingly angled flat surfaces (labeled 420*a–c* in the '356 application) of the inserter/impactor, and operation of the inserter/impactor pulls the holding pin toward the flat surface of the inserter/impactor opposite the pin, to rigidly hold the static trial 1000 (or disc) by the structure of the static trial 1000 (or disc) having the hole 1220*b* (e.g., the baseplate 108*b*). When the static trial 1000 (or disc) is held in this manner, rotation of the static trial 1000 (or disc) about a longitudinal axis (of the static trial 1000 (or disc)) relative to the inserter/impactor is prevented by interference of the corners of the static trial's 1000 (or disc's) flat surfaces 1200*a–c* and the corners of the inserter/impactor's flat surfaces, similar to the manner in which a wrench holding a nut prevents rotation of the nut relative to the wrench. Further, the holding of the static trial 1000 (or disc) in this manner allows for some repositioning of the static trial 1000 (or disc) in the intervertebral space via rotation of the static trial 1000 (or disc) in either direction about the longitudinal axis of the intervertebral space.

Preferably, both of the baseplates of the static trial 1000 (or disc) have similarly configured flat surfaces. For example, the lower baseplate's 1080*b* flat surfaces 1200*a–c* have similarly configured and similarly oriented counterpart flat surfaces 1200*d–f* on the upper baseplate 1080*a*. Further preferably, both baseplates' 1080*a–b* flat surfaces 1200*a–f* face the angled flat surfaces of the inserter/impactor when the static trial 1000 (or disc) is held by the inserter/impactor. For example, as discussed below with regard to the inserter/impactor, in an anterior approach for the trial 1000 (and as can be seen and understood from FIGS. 4*e–h* of the '356 application in that the same shows the inserter/impactor against the static trial 100 described therein (which has a flat surface and hole configuration identical to that of the static trials 1000 described herein)), 1200*a* and 1200*d* facing 420*a*, 1200*b* and 1200*e* facing 420*b*, and 1200*c* and 1200*f* facing 420*c*.

It should be noted that preferably, when the static trial 1000 is held by the inserter/impactor, the flat surfaces 1200*a–c* and the counterpart flat surfaces 1200*d–f* are tightly held against the angled flat surfaces of the inserter/impactor as described above. It is also preferable that the baseplates 1080*a–b* of each of the plurality of static trials 1000 be appropriately lordotically angled relative to one another to ease insertion of the static trial 1000 into the intervertebral space and to mimic how the artificial intervertebral disc will typically be oriented as it is being inserted using the inserter/impactor, and to ease insertion of the static trial 1000 into the intervertebral space. While not shown in FIGS. 1*a–f*, in some embodiments, when the static trials 1000 are formed in such a lordotically oriented configuration, it is preferable that the flat surfaces 1200*d–f* on the first (e.g., upper) baseplate 1080*a* be parallel to the flat surfaces 1200*a–c* of the second (e.g., lower) baseplate 1080*b* in the static trial's 1000 appropriately lordotically oriented configuration, so that when the static trial 1000 is held tightly by the inserter/impactor, the flat surfaces 1200*a–f* are flush with the flat surfaces of the inserter/impactor even though the baseplates 1080*a–b* are lordotically angled with respect to one another.

Also preferably, in order to provide for a holding of the static trial 1000 (or disc) for two additional (here, anteriolateral) insertion approaches, each static trial 1000 (or disc) also includes two additional holes 1220*a* and 1220*c*, one (e.g., 1220*a*) spaced apart from one of the anteriolaterally facing flat surfaces (e.g., 1200*a*), and the other (e.g., 1220*c*) spaced apart from the other of the anteriolaterally facing flat surfaces (e.g., 1200*c*). Accordingly, operation of the inserter/impactor can fit the holding pin into either of these two additional holes 1220*a* or 1220*c*, and hold the associated anteriolaterally facing flat surface (the one associated with the hole into which the pin is fit) of the static trial 1000 (or disc) against the flat surface of the inserter/impactor opposite the pin. For example, as discussed below with regard to the inserter/impactor, in a first anteriolateral approach for the trial 1000 (and as can be seen and understood from FIG. 4*i* of the '356 application in that the same shows the inserter/impactor against the static trial 100 described therein (which has a flat surface and hole configuration identical to that of the static trials 1000 described herein)), 1200*a* and 1200*d* facing 420*b*, 1200*b* and 1200*e* not confronted, and 1200*c* and 1200*f* facing 420*a*. And, for example, as discussed below with regard to the inserter/impactor, in a second anteriolateral approach for the trial 1000 (and as can be seen and understood from FIG. 4*j* of the '356 application in that the same shows the inserter/impactor against the static trial 100 described therein (which has a flat surface and hole configuration identical to that of the static trials 1000 described herein)), 1200*a* and 1200*d* facing 420*c*, 1200*b* and 1200*e* facing 420*a*, and 1200*c* and 1200*f* not confronted.

It should be understood that preferably, in order to facilitate these additional approaches, the angle separating the anteriorly facing flat surface of the static trial 1000 (or disc) and one of the anteriolaterally facing flat surfaces of the static trial 1000 (or disc) is equal to the angle separating the anteriorly facing flat surface and the other of the anteriolaterally facing flat surfaces. Preferably, the surfaces are angled with respect to one another at an angle of 33.4 degrees.

It should also be understood that the inclusion of additional adjacent angulated surfaces and/or additional notches (or placing the angulated surfaces or notches in other locations on the trial (or disc)), and/or including corresponding holes adjacent to such angulated surfaces, can provide the surgeon with additional approaches, e.g., other anteriolateral approaches, directly lateral approaches, posteriolateral approaches, and/or directly posterior approaches. For example, a trial (or disc) can have angled surfaces (and corresponding holes) along the entire perimeter of one or both of the baseplates, and thus enable the surgeon to engage the trial (or disc) from a number of angles, including anterior, posterior, lateral, anteriolateral, and posteriolateral angles. Or, for example, a trial (or disc) can have notches located on directly laterally facing surfaces or posterior surfaces or posterior-laterally facing surfaces, and thus enable the surgeon to engage the trial (or disc) with the static trial holder from a number of angles, including anterior, posterior, lateral, anteriolateral, and posteriolateral angles. (It should be noted that, while the opposing notches of the static trials are shown formed in conjunction with the angulated surfaces of the baseplates, neither the number nor the placement of the opposing notches need coincide or be related to the number or placement of the angulated surfaces of the baseplates. For example, the notches can be applied to a trial or disc having curved approach surfaces.)

Additionally with regard to features that can be engaged by a tool, each of the static trials 1000 includes at least one feature that can be engaged by a tool that preferably is also used to engage the artificial intervertebral disc that the trial approximates. Suitable tools that can grip both the trial and the artificial intervertebral disc include, but are not limited to, the repositioners/extractors described in the '356 application. Specifically, for being engaged by the repositioners/extractors, each static trial 1000 (or disc) includes at least two holes extending longitudinally into one of the baseplates of the static trial 1000 (or disc) from the inwardly facing surface of the baseplate. More than two holes can be used to provide for multiple repositioning/extracting approaches. Preferably, in order for the same repositioning/extracting tool to be used for multiple approaches on the same trial or artificial intervertebral disc, adjacent holes should be separated by the same distance separating other adjacent holes.

As discussed in greater detail in the '356 application with regard to the repositioners/extractors, in order to engage two of the holes, each repositioner/extractor has two pins extending in parallel from a central shaft, perpendicular to the longitudinal axis of the central shaft. The pins are spaced to engage the two holes simultaneously, and each pin has a diameter smaller than the diameter of the hole it is to engage. Therefore, the pins can be inserted into the holes, and pulling or pushing on the central shaft along its longitudinal axis when the holes are engaged pulls or pushes the static trial or artificial intervertebral disc in the intervertebral space. Further, because two holes are engaged, the static trial or artificial intervertebral disc can be rotated in either direction about a longitudinal axis passing through the intervertebral space, by rotating of the central shaft of the repositioner/extractor about its distal end, about an axis parallel to the longitudinal axes of the pins. A handle at a proximal end of the central shaft is useful for pushing or pulling on the shaft. A flange adjacent the proximal end of the shaft is useful for impaction (either with a distally directed force or a proximally directed force), if necessary to manipulate the shaft.

On each repositioner/extractor, the pins are formed on prongs that extend laterally from the central shaft. The direction of the prongs, and the location of the pins relative to the central shaft, determine the angle or angles of surgical approach for which a particular repositioner/extractor can be used. Further, the number and location of holes further determine the angle or angles of surgical approach for which a particular repositioner/extractor can be used. Accordingly, the present invention contemplates a variety of repositioner/extractors, and a variety of holes configurations, to provide the surgeon with a variety of possible surgical approach angles. For example, three repositioner/extractors (symmetric, offset left, and offset right) and two hole configurations are illustrated and described in greater detail in the '356 application. The first hole configuration described therein is illustrated herein on each baseplate 1080a,1080b of the static trials 1000 described herein. That is, referring again to FIGS. 1a–f, the first hole configuration includes the hole configuration described above, that is, three holes on one of the baseplates (e.g., the lower baseplate 1080b), the holes being configured so that a first hole 1220b is located in the anterior-posterior plane, and the adjacent (second 1220a and third 1220c) holes are located in respective opposing anteriolateral planes on either side of the first hole 1220b. The upper baseplate 1080a also includes three similarly configured holes 130a–c as shown. While the second hole configuration illustrated and described in the '356 application (or any other hole configuration) is not illustrated herein, it should be understood that the static trials 1000 can be configured with such second hole configuration, or any other hole configuration, without departing from the scope of the present invention. (It should be noted that, while the opposing notches of the static trials 1000 are shown formed in conjunction with the holes in the baseplates, neither the number nor the placement of the opposing notches need coincide or be related to the number or placement of the holes in the baseplates.)

It should be understood that configurations having more or fewer holes, and in a variety of locations, are contemplated by the invention, and the detailed descriptions of only two hole configurations is not meant to limit the invention to only these two configurations. Importantly, the invention encompasses using a hole or any number of holes, bored at any suitable angle, whether parallel to other holes or not, in any number of locations on a spacer, a trial or an artificial intervertebral disc (not limited to locations on the baseplates), for purposes of enabling the spacer, trial, or disc to be engaged by a manipulation instrument (not limited to a repositioner/extractor) that engages the hole, and/or to enable the surgeon to work from a variety of approaches. For example, as described in more detail below, the first and second hole configurations described in the '356 application and herein, in cooperation with the repositioner/extractors, provide the surgeon with the ability to work from a directly anterior approach, as well as several anteriolateral approaches. It should be understood that additional hole configurations can enable the surgeon to work from a directly posterior approach, posteriolateral approaches, directly lateral approaches, or anteriolateral approaches that are different than those illustrated. For example, the placement of one or more suitably spaced holes (or the addition of one or more holes) on the posterior edge, and/or one or both of the lateral edges of one or both of the baseplates, would enable the surgeon to use the repositioner/extractors of the present invention to achieve such approaches.

Thus, it can be seen that each of the repositioner/extractors can be used in more than one manner depending on the tool desired and the approach desired. These manners are described in greater detail in the '356 application and illustrated in FIGS. 5p-dd of the '356 application with regard to the detailed description of the repositioners/extractors.

Also preferably, the baseplates 1080a–b of each of the plurality of static trials 1000 preferably has a convex dome 1240a–b on its outwardly facing surface 1260a–b that is shaped like a convex dome on an outwardly facing surface of the corresponding baseplate of the artificial intervertebral disc that the static trial 1000 approximates (e.g., the artificial intervertebral disc 160 described in the '356 application). Preferably, each convex dome 1240a–b is smooth, rather than having a porous coating that is preferred for the convex domes of the artificial intervertebral disc 160, and each outwardly facing surface 1260a–b does not have stabilizing spikes such as the stabilizing spikes on the outwardly facing surfaces of the artificial intervertebral disc 160. The omission of these device stabilizing and bone ingrowth encouraging structures and surfaces on the static trials 1000 enables the surgeon to test the size of the artificial intervertebral disc to be implanted without traumatically engaging the vertebral body endplates.

Accordingly, the surgeon can prepare and distract the intervertebral space, and then insert and remove at least one of the static trials (or more, as necessary) to find the size that is most appropriate for the intervertebral space.

A preferred embodiment of a static trial holder of the present invention will now be described.

Referring to FIGS. 2a–c and 2k, a static trial holder of the present invention is shown in side (FIG. 2a), top (FIG. 2b), perspective (FIG. 2c), and side cutaway (FIG. 2k) views. In addition, referring to FIGS. 2d1, 2d2, 2d3, and 2e–f, a sleeve of the static trial holder is shown in side (FIG. 2d1), top (FIG. 2d2), side cutaway (FIG. 2d3), front (FIG. 2e), and back (with partial cutaway) (FIG. 2k) views. In addition, referring to FIGS. 2g–i, an extension of the static trial holder is shown in top (FIG. 2g), proximal cutaway (FIG. 2h), side (FIG. 2i), and distal cutaway (FIG. 2j) views.

The static trial holder 2000 is provided primarily for use in holding, inserting and removing the static trials 1000 described herein, the static trials 100 described in the '356 application, or other static trials or distraction spacers having suitable features therefor, such as the distraction spacers disclosed in the '127 application.

More specifically, the static trial holder 2000 includes a handle 2020, an extension 2040, and a sleeve 2060. As shown in FIG. 2k, the handle 2020 and the extension 2040 are fixed to one another (preferably by the distal end of the handle 2020 being fixed to the proximal end of the extension 2040) to form a shaft 2080. The sleeve 2060 surrounds the extension 2040 and is rotatable with respect to the handle 2020 and the extension 2040 about the longitudinal axis of the shaft 2080. The handle 2020 preferably has an flange 2320 at its proximal end for use in applying a distally or proximally directed force to get the static trial 1000 (or distraction spacer) into or out of the intervertebral space, and/or for use in helping the surgeon rotate the sleeve 2060 with respect to the extension 2040 (by gripping the flange 2320 and the control knob 2190 described below).

The distal end of the extension 2040 forms a contractable and expandable holding enclosure 2100 in that the distal end is divided at a fulcrum 2120 into two prongs 2140a–b, each of which terminates in a semicircular extent 2160a–b, each of which has a tapered end 2150a–b. The extents 2160a–b are oriented such that the tapered ends 2150a–b face one another to define a radially inwardly tapering mouth 2130, and such that the semicircular openings oppose one another to define the holding enclosure 2100. The prongs 2140a–b are spring biased toward a neutral position (preferably by the formation of the fulcrum 2120 in combination with the strength of the material of which the extension 2040 is made) such that the holding enclosure 2100 is spring biased to a receptive state (described below), but the prongs 2140a–b can be brought together to contract the holding enclosure 2100 to a contracted state, (described below) or the prongs 2140a–b can be further separated to expand the holding enclosure 2100 to an expanded state (described below).

When the holding enclosure 2100 is in the receptive state, the width of the mouth 2130 of the holding enclosure 2100 does not accommodate the diameter of the cylindrical trunk 1060 of the static trial 1000 (or distraction spacer) for passage therethrough. However, from this receptive state, the mouth 2130 can be temporarily widened (placing the holding enclosure 2100 in its expanded state) to accommodate the diameter (for passage of the cylindrical trunk 1060 through the mouth 2130), if a sufficient force is applied to overcome the neutral position bias of the prongs 2140a–b and thus widen the mouth 2130. (Preferably, there is enough space between the outer surfaces of the prongs 2140a–b and the inner surface of the bore 2180 of the sleeve, when the prongs 2140a–b are in their neutral position, so that the prongs 2140a–b can be separated without interference.) The sufficient force can be applied by pressing the cylindrical trunk 1060 against the tapered ends 2150a–b of the mouth 2130, in that the separating force component of the radially inward force of the pressing will be applied to the semicircular extents 2160a–b by the taper of the tapered ends 2150a–b. Because the holding enclosure 2100 is biased toward the receptive state, after the cylindrical trunk 1060 is passed through the mouth 2130 and into the holding enclosure 2100, the holding enclosure 2100 will return to its receptive state in which the width of the mouth 2130 does not allow passage of the cylindrical trunk 1060 without the sufficient force. Preferably, the force required to widen the mouth 2130 is greater than gravity and/or the greatest force that will be experienced by moving the static trial holder 2000 prior to placing the holding enclosure 2100 in the contracted state. Therefore, once the cylindrical trunk 1060 is in the holding enclosure 2100, even before the holding enclosure 2100 is placed in its contracted state, the cylindrical trunk 1060 will not escape the holding enclosure 2100 as the static trial holder 2000 is oriented with the holding enclosure 2100 downward, or is moved about.

It should be understood that when the static trial 1000 (or distraction spacer) is being held (either when the holding enclosure 2100 is in its receptive state or in its contracted state discussed below), because the semicylindrical extents 2160a–b fit within the annular groove 1040 of the static trial 1000 (or distraction spacer), the static trial 1000 (or distraction spacer) will not escape from the enclosure along the longitudinal axis of the cylindrical trunk 1060. That is, as noted above, the recess 1020 of each static trial 1000 (or distraction spacer) forms an annular groove 1040 that establishes the cylindrical trunk 1060 between the baseplates of the static trial (or distraction spacer), such that the baseplates extend as flanges from either end of the cylindrical trunk 1060. Accordingly, preferably, the opposing semicircular extents each have a thickness smaller than the width of the annular groove 1040, and as such fit into the annular groove 1040 to grip the cylindrical trunk 1060 between them.

In some embodiments, while not shown in FIGS. 1a–f or FIGS. 2a–k, it is preferable that the annular groove 1040 radially widen outwardly, such that the walls of the annular groove 1040 taper toward one another with the increasing depth of the groove, such that the floor of the groove is more narrow than the opening 1160 of the groove. Accordingly, preferably, in such embodiments, each semicircular extent 2160a–b correspondingly radially widens outwardly, such that the thinner portion of the extent 2160a–b fits closer to the floor of the annular groove 1040, so that the tapered surfaces 2150a–b of the extents 2160a–b compress against the tapered walls of the annular groove 1040 when the static trial 1000 is gripped by the static trial holder 2000. This taper locking provides for a secure grip so that the static trial 1000 can be manipulated accurately and efficiently.

In some embodiments, while not shown in FIGS. 1a–f or FIGS. 2a–k, it is also preferable that the floor of the annular groove 1040 of the cylindrical trunk 1060 be ridged (e.g., have ridges that run parallel to the longitudinal axis of the cylindrical trunk), and the surfaces of the semicircular extents 2160a–b of the static trial holder 2000 that compress against the floor of the annular groove 1040 when the static trial holder 2000 grips the static trial 1000 be correspondingly provided with ridges. The interlocking of the ridges of the static trial 1000 with the ridges of the static trial holder 2000 when the static trial 1000 is gripped prevents rotation of the static trial 1000 about the longitudinal axis of the cylindrical trunk 1060 with respect to the static trial holder 2000.

In order to more tightly hold the static trial 1000 (or distraction spacer) for manipulation of the static trial 1000 (or distraction spacer) during surgical procedures in which greater forces will be experienced by the static trial 1000 (or distraction spacer) and the static trial holder 2000, the holding enclosure 2100 can be placed in a contracted state. The holding enclosure 2100 can be considered "unlocked"

in its receptive or expanded states, and "locked" in its contracted state, with respect to the nature of the hold that the static trial holder 2000 potentially can have or has on the cylindrical trunk 1060. Preferably, when the holding enclosure 2100 is locked, a force greater than that which is applicable by an unaided surgeon or nurse (i.e., that which can be applied to remove the cylindrical trunk 1060 from the holding enclosure 2100 when the holding enclosure 2100 is in its receptive state), and greater than that which will be experienced by the static trial 1000 (or distraction spacer) and the static trial holder 2000 during surgical procedures) would be required to pull the cylindrical trunk 1060 out of the holding enclosure 2100. The placement of the holding enclosure 2100 in its locked state or unlocked state is effected by operation of a holding assembly that includes the extension 2040 and the sleeve 2060 and the manner in which they are configured and interact.

More particularly, the prongs 2140a–b can be brought together (or brought closer to one another; it should be understood that they need not touch to be encompassed by the present invention), to lock the holding enclosure 2100, by a rotation of the sleeve 2060 with respect to the handle 2020 and the extension 2040 about the longitudinal axis of the shaft 2080. A rotation control knob 2190 is provided to ease the rotation of the sleeve 2060. As shown in FIGS. 2g and 2i–j in view of FIGS. 2d1, 2d2, 2d3, and 2e, the bore 2180 of the sleeve 2060 (shown in front view in FIG. 2e) defines a cross-section that has a width 2200 that is greater than its depth 2220. Further as shown in those figures, the prongs 2140a–b when separated (shown in cutaway in FIG. 2j) define a cross-section having a width 2240 that is greater than its depth 2260, the width 2240 and depth 2260 of the prongs' cross-section being closely accommodated by the width 2200 and depth 2220 of the bore's cross-section. When the prongs 2140a–b are together, the width of prongs' cross-section is closely accommodated by the depth 2220 of the bore's cross-section. Thus, when the sleeve 2060 is rotated with respect to the extension 2040, the sides of the bore defining the depth 2220 of its cross-section bear against the sides of the prongs 2140a–b defining the width of their cross-section.

It should be noted that in order to ease the rotation of the sleeve 2060 so that the sides of the bore 2180 can bear against the sides of the prongs 2140a–b, the corners of the bore 2180 are radiused, and at least the sides (that face away from one another) of the prongs 2140a–b are curved. Preferably, as shown, the prongs 2140a–b when separated define a partial cylindrical cross-section. The effect of the bearing (of the sides of the bore 2180 against the sides of the prongs 2140a–b) is borne by the space between the prongs 2140a–b, so that the space narrows and the prongs 2140a–b are brought toward one another until they are accommodated within the bore's depth 2220. The bringing together of the prongs 2140a–b brings the semicircular extents 2160a–b together to place the holding enclosure 2100 into its contracted state, locking it.

The movement of the sleeve 2060 toward positions that will either unlock or lock the holding enclosure 2100, and the stopping of the sleeve 2060 at such positions, is effected by the inclusion of at least one groove 2280 that extends in a 90 degree arc on the outer surface of the extension 2040, and at least one radial bore 2300 through the wall of the sleeve 2060 (preferably through the rotation control knob 2190 as shown), which bores 2300 each have secured therein a dog headed screw (not shown) so that a head of the screw protrudes into interior of the sleeve (it should be understood that functionally equivalent devices can also be used in place of a dog headed screw). Preferably, each groove 2280 is associated with a respective cooperating bore 2300 and dog headed screw. When a given bore 2300 (and dog headed screw) is aligned with an end of its associated groove 2280, the sleeve 2060 is in a position at which the holding enclosure 2100 is either unlocked or locked (unlocked when the head of the screw is positioned at one end of the groove, locked when it is positioned at the other end of the groove). The head of the dog headed screw protrudes into the interior of the sleeve and into the groove 2280 and rides therein as the sleeve 2060 is rotated. When an end of the groove 2280 is reached by the head of the screw, the head of the screw stops against the wall of the groove 2280 at the end of the groove 2280, stopping the rotation of the sleeve 2060, and setting the holding enclosure 2100 to either the unlocked or locked position. In order to set the holding enclosure 2100 to the alternative position, the sleeve 2060 is reverse rotated, causing the head of the screw to ride in the groove 2280 in the opposite direction toward the other end of the groove 2280. When the head of the screw reaches the other end of the groove 2280, the head of the screw stops against the wall of the groove 2280 at that end of the groove 2280, stopping the rotation of the sleeve 2060, and setting the holding enclosure 2100 to the alternative position.

Further, the sleeve 2060 preferably has on its exterior surface at least one stop protrusion 1380 that is positioned and dimensioned to extend dorsally or ventrally from the exterior surface when the holding enclosure is in its "locked" state (see FIGS. 3a–f), so that when the surgeon inserts the static trial 1000 into the intervertebral space, the stop protrusions 1380 prevent the static trial 1000 from being inserted too far into the space (that is, so that the stop protrusions 1380 hit against the lips of the adjacent vertebral body endplates before the static trial 1000 is inserted too far).

Accordingly, as shown with reference to FIGS. 3a–f, the static trials 1000 of the invention (or distraction spacers such as those disclosed in the '127 application) can be held and manipulated with the static trial holder 2000 from a variety of approach angles. Holding the handle 2020 of the static trial holder 2000 in one hand, an operator can push the cylindrical trunk 1060 of the static trial 1000 (or the distraction spacer) against the mouth 2130 of the holding enclosure 2100 with enough force to temporarily expand the mouth 2130 to a width that will accommodate the diameter of the cylindrical trunk 1060 for passage through the mouth 2130. The radially inward tapering of the sides of the mouth 2130 (the facing ends 2150a–b of the semicircular extents 2160a–b of the prongs 2140a–b) facilitates this insertion. It should be noted that, as shown in FIGS. 3a–f with reference to FIGS. 1a and 2j, the depth 2260 of the prongs' cross-section is closely accommodated by the depth of the opening establishing by the width of the annular groove 1020 and the depths 1340 of the notches in the pair of opposing notches (1320a,d, 1320b,d, or 1320c,f), and the width 2240 of the prongs' cross-section is accommodated by the width 1360 of the notches in the pair of opposing notches (1320a,d, 1320b,d, or 1320c,f), so that the prongs' cross-section fits into the opposing notches as, and when, the cylindrical trunk 1060 is surrounded by the semicircular extents 2160a–b. (That is, that the width 1360 of the notch pair accommodates the width 2240 of the static trial holder's 2000 prongs' 2140a–b cross-section even when the prongs 2140a–b are separated to place the holding enclosure 2100 in an expanded state as described below. This enables the notch pair to accommodate the width 2240 of the prongs' cross-section as the cylindrical trunk 1060 of the static trial 1000 is being snapped into the holding enclosure 2100.)

Once the cylindrical trunk 1060 has passed into the holding enclosure 2100, the operator can let go of the static trial 1000 (or distraction spacer) because the prongs 2140a–b will be overcome by their bias toward their neutral state and thus hold the static trial 1000 in the holding enclosure 2100 to prevent the static trial 1000 from falling out or slipping out as the static trial holder 2000 is moved with the static trial 1000 prior to closing (e.g., locking) the holding enclosure 2100. (When the static trial 1000 (or distraction spacer) is being held in this manner, and the holding enclosure 2100 is unlocked, the static trial 1000 can be removed from the holding enclosure 2100 by a pulling of the static trial 1000 through the mouth 2130 of the holding enclosure 2100 with a force required to again temporarily overcome the bias of the prongs 2140a–b toward their neutral state, to separate them and make the width of the mouth 2130 accommodate the diameter of the cylindrical trunk 1060.)

Once the operator is ready to lock the holding enclosure 2100, while still gripping the handle 2020 of the static trial holder 2000, he rotates the rotation control knob 2190 clockwise (or counterclockwise depending on how the grooves 2280 are configured; that is, they are illustrated as being configured to enable a locking with a clockwise rotation, and an unlocking with a subsequent counterclockwise rotation, although other embodiments can enable a locking with a counterclockwise rotation, and an unlocking with a clockwise rotation, to accommodate left-handed persons or right-handed persons or for other reasons) to rotate the sleeve 2060 ninety degrees to the next position. As the sleeve 2060 rotates, the head of the dog headed screw rides freely in the groove 2280, and the sides of the sleeve's bore's inner surface bear against the curved outer surfaces of the prongs 2140a–b to push the prongs 2140a–b together so that they are accommodated by the depth 2220 of the bore 2180. As the dog headed screw reaches the end of the groove 2280, the prongs 2140a–b are pressed against one another and the semicircular extents 2160a–b move toward one another. The prongs 2140a–b are held in and biased toward the closed position, and the semicircular extents 2160a–b are correspondingly maintained together about the cylindrical trunk 1060, by the fitting of the bore's surfaces against the prongs' surfaces. When the prongs 2140a–b are held in this manner, the cylindrical trunk 1060 cannot be removed through the mouth 2130 of the now-tighter (e.g., locked) holding enclosure 2100 without the application of forces preferably greater than will be encountered when inserting and removing the static trial 1000 from the intervertebral space during the surgical procedures.

Further, the interference between the prongs 2140a–b and the opposing notches in the notch pair in which the prongs 2140a–b are disposed prevents rotation of the static trial 1000 about a longitudinal axis (e.g., an axis parallel to the longitudinal axis of the cylindrical trunk 1060) with respect to the static trial holder 2000. That is, if the static trial 1000 is encouraged, by forces encountered during manipulation of the static trial 1000, to rotate about such an axis with respect to the static trial holder 2000, the side walls of the notches will be confronted by the prong 2140a–b bodies and such rotational movement of the static trial 1000 will be stopped. (As can be seen in the FIGS. 3a–f, the prongs 2140a–b are too deep to fit into the annular groove 1060 without the notch pair accommodating their depth.) The same will happen if a reverse rotation about such an axis is attempted.

Figure 3A:
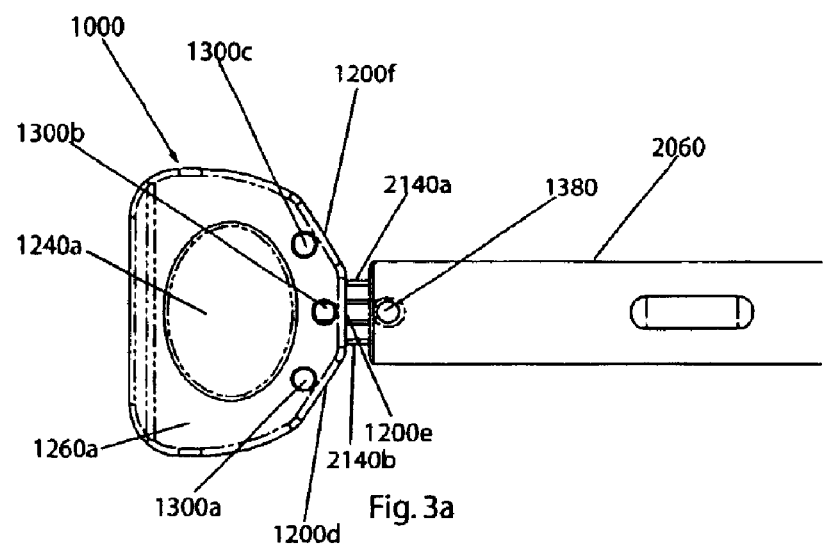
FIGS. 3a–d show top (FIG. 3a), side (FIG. 3b), and perspective (FIG. 3c) views of the static trial holder of FIGS. 2a–k holding a static trial of FIGS. 1a–f from an anterior approach hold.
Figure 3B:
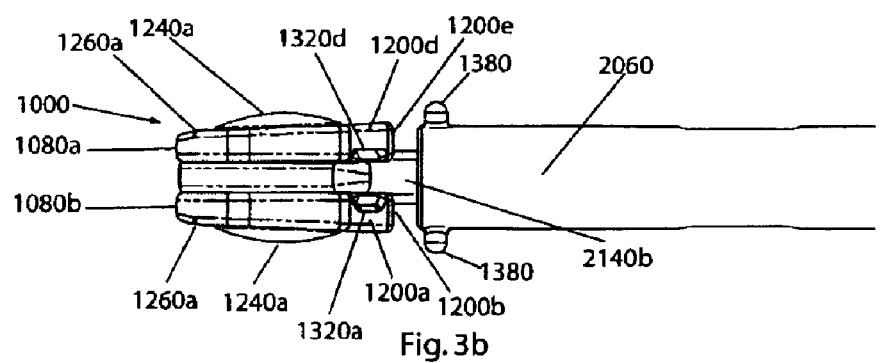
Figure 3C:
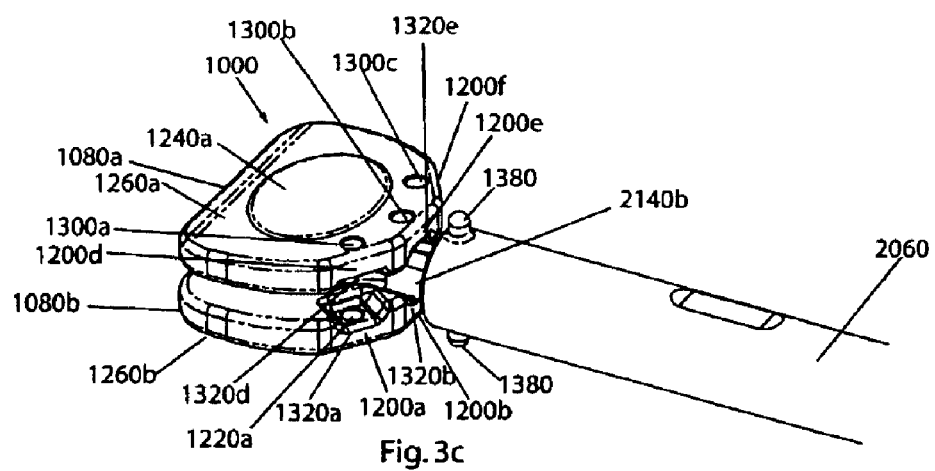
Figure 3D:
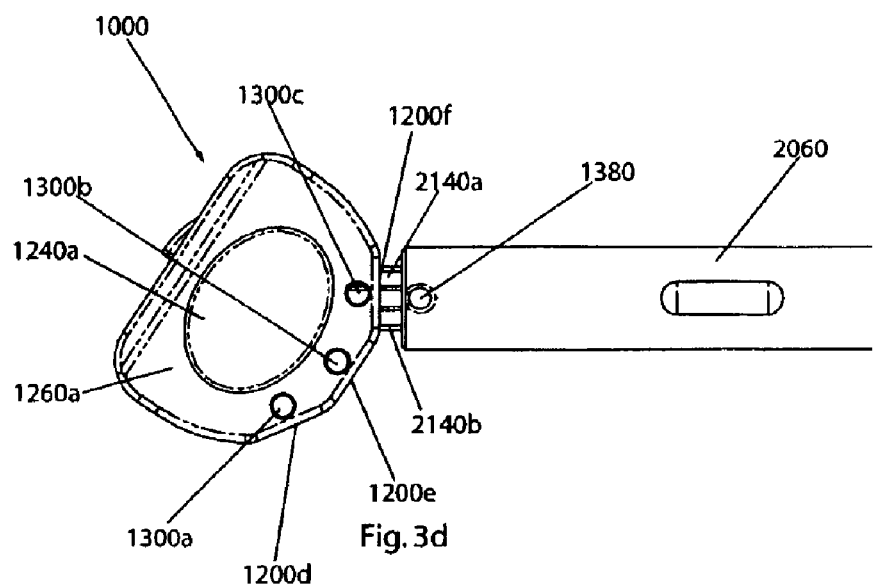
Figure 3E:
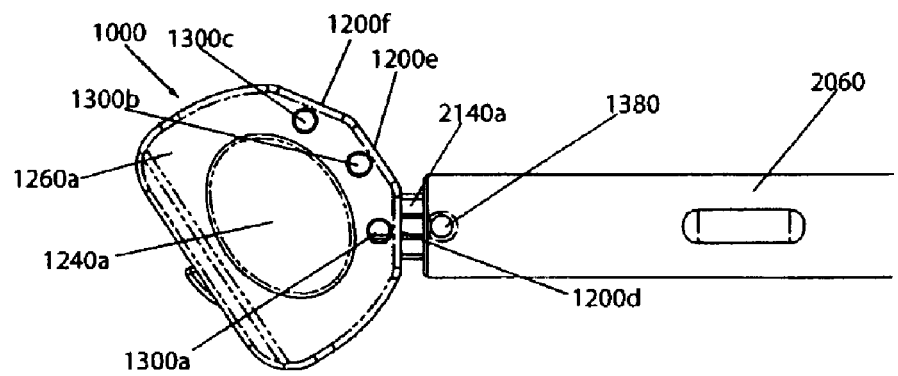
Figure 3F:
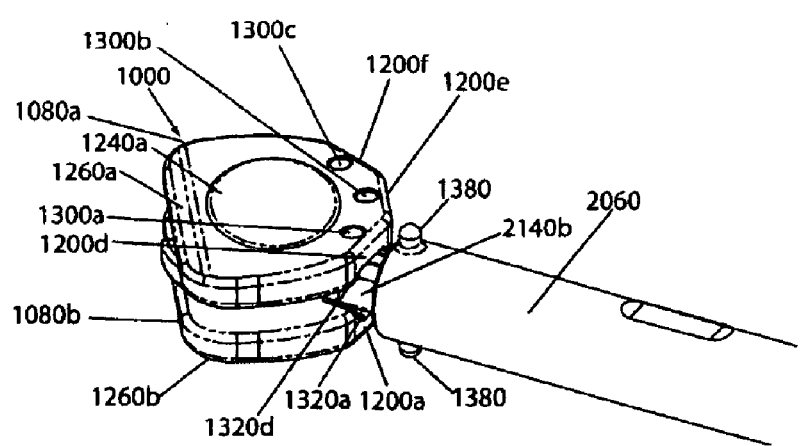
FIG. 3f shows a perspective view of the static trial holder of FIGS. 2a–k holding a static trial of FIGS. 1a–f from the anterior-lateral approach hold of FIG. 3e.

Once the static trial 1000 has been inserted and removed from the intervertebral space (or the distraction spacer has been inserted and removed from the intervertebral space after being used to distract the space), the operator can unlock the holding enclosure 2100 by reverse rotating the sleeve 2060 (with enough initial force to overcome the biasing of the fitting of the bore's and the prongs' surfaces) ninety degrees. Again, as the sleeve 2060 rotates, the sides of the sleeve's bore's inner surface move away from the curved outer surfaces of the prongs 2140a–b and allow the prongs 2140a–b to separate (under their own bias toward the neutral position) as they are accommodated by the width 2200 of the bore 2180. When the prongs 2140a–b are separated and allowed to remain in that position by the maintenance of the sleeve 2060 in the new position (with the head of the dog headed screw against the wall of the groove 2280 at the other end of the groove 2280), the semicircular extents 2160a–b are separated from one another and hold the cylindrical trunk 1060 against falling or slipping out. That is, the cylindrical trunk 1060 can be removed by the operator if the operator applies a sufficient force to widen the mouth 2130 of the holding enclosure 2100 enough to let the cylindrical trunk 1060 pass through the mouth 2130. Once the static trial 1000 (or distraction spacer) is removed, another one can be inserted and manipulated if required. As shown in FIGS. 3d–f, in addition to the anterior approach angle shown in FIGS. 3a–c, the illustrated notch configuration accommodates two anterior-lateral approach angles as well.

Accordingly, the static trial holder 2000 can be used to insert and remove the distraction spacers of the '127 application to distract the intervertebral space as described in the '127, and thereafter (or during the distraction) hold to insert and remove the static trials 1000 to find the appropriate size of artificial intervertebral disc to be implanted.

While there has been described and illustrated specific embodiments of instrumentation, it will be apparent to those skilled in the art that variations and modifications are possible without deviating from the broad spirit and principle of the invention. The invention, therefore, shall not be limited to the specific embodiments discussed herein.

What is claimed is:

1. An instrumentation set for evaluating an intervertebral space, the set comprising:

a plurality of trial artificial intervertebral discs, each of which approximates at least a size and a shape of a corresponding one of a plurality of artificial intervertebral discs, one of which plurality of artificial intervertebral discs is to be implanted into the intervertebral space, each of the trials including spaced apart baseplates and a perimetrical groove that establishes a trunk between the baseplates such that the baseplates extend as flanges from either end of the trunk; and a trial artificial intervertebral disc holder suitable for holding any of the trials, the trial holder including a shaft, a sleeve, and a selectively openable and closeable holding enclosure defined by opposing extents at a distal end of the shaft, into which holding enclosure any of the trials is capturable, each of the extents being thinner than a width of the perimetrical groove such that they fit into the perimetrical groove to engage the trunk, the shaft having a portion proximal to the extents that is thicker than the width of the perimetrical groove such that the proximal portion is prevented from fitting into the perimetrical groove;

wherein each of the trials further includes opposing recesses adjacent and communicating with the perimetrical groove, one being formed in one of the baseplates and another being formed in the other of the baseplates opposite the one recess, that define a volume dimensioned to accommodate a longitudinal portion of the proximal portion; and wherein when the trial is engaged by the trial holder so that the extents are fitted within the perimetrical groove to engage the trunk between them, the volume defined by the opposing recesses accommodates the longitudinal portion of the proximal portion such that rotation of the trial about an axis perpendicular to the longitudinal axis of the shaft is limited by interference between the longitudinal portion and the opposing recesses.

2. The instrumentation set of claim 1, wherein the perimetrical groove is an annular groove, the trunk is a cylindrical trunk, and the extents are semicircular.

3. The instrumentation set of claim 1, wherein the shaft of the trial holder has a distal portion that divides to form first and second prongs separated by a distance, each prong having one of the extents at a distal end of the prong, the prongs being spring biased toward a neutral position such that the holding enclosure is spring biased toward a receptive state, in which receptive state the trunk is snappable into and out of the holding enclosure.

4. The instrumentation set of claim 3, wherein the trunk is snappable into and out of the holding enclosure by a forcing of the trunk through a mouth of the holding enclosure with enough force to overcome the spring bias of the prongs to expand the mouth to a width that accommodates a diameter of the trunk.

5. The instrumentation set of claim 4, wherein the sleeve surrounds the prongs and has an inner surface configured to press the prongs toward one another when the sleeve is rotated about the longitudinal axis of the shaft and to allow the prongs to separate under their spring bias toward the neutral position when the sleeve is reverse rotated about the longitudinal axis of the shaft, such that the holding enclosure is placeable into a contracted state by the rotation of the sleeve, in which contracted state the trunk is held so that the trial will not escape the holding enclosure during insertion and removal from the intervertebral space, and placeable into the receptive state by the subsequent reverse rotation of the sleeve.

6. The instrumentation set of claim 5, wherein an outer surface of the shaft includes at least one arc groove in which a protrusion on the inner surface of the sleeve rides during the rotation and the reverse rotation of the sleeve, a placement of the protrusion at one end of the groove corresponding with a placement of the holding enclosure in the contracted state, a placement of the protrusion at the other end of the groove corresponding with a placement of the holding enclosure in the receptive state.

7. The instrumentation set of claim 5, wherein the inner surface of the sleeve forms a bore having a cross-section having a width that is greater than its depth, and the prongs when separated define a cross-section having a width that is greater than its depth, the width and depth of the prongs' cross-section when the prongs are separated being closely accommodated by the width and depth of the bore's cross-section, the width of the prongs' cross-section when the prongs are together being closely accommodated by the depth of the bore's cross-section, such that when the sleeve is rotated, sides of the bore defining the depth of its cross-section bear against sides of the prongs defining the width of their cross-section to narrow the distance between the prongs until they are together.

8. The instrumentation set of claim 1, wherein the sleeve has on an exterior surface at least one protrusion that is positioned and dimensioned to extend from the exterior surface when the holding enclosure is closed such that when a surgeon inserts the trial into the intervertebral space using the trial holder, the protrusion prevents the trial from being inserted too far into the intervertebral space because of an interference between the protrusion and an adjacent vertebral body.

9. The instrumentation set of claim 1, wherein an outer surface of the shaft includes at least one arc groove in which a protrusion on an inner surface of the sleeve rides during rotation of the sleeve, a placement of the protrusion at one end of the groove corresponding with a closing of the holding enclosure, a placement of the protrusion at the other end of the groove corresponding with an opening of the holding enclosure.

10. The instrumentation set of claim 1, wherein the shaft of the trial holder has a distal portion that divides to form first and second prongs separated by a distance, each prong having one of the extents at a distal end of the prong, the prongs being spring biased toward a position in which the holding enclosure is open.

11. The instrumentation set of claim 10, wherein the sleeve surrounds the prongs and has an inner surface configured to press the prongs toward one another when the sleeve is rotated about the longitudinal axis of the shaft and to allow the prongs to separate under their spring bias when the sleeve is reverse rotated about the longitudinal axis of the shaft, such that the holding enclosure is closeable by the rotation of the sleeve, and openable by the reverse rotation of the sleeve.

12. The instrumentation set of claim 11, wherein the inner surface of the sleeve forms a bore having a cross-section having a width that is greater than its depth, and the prongs when separated define a cross-section having a width that is greater than its depth, the width and depth of the prongs' cross-section when the prongs are separated being closely accommodated by the width and depth of the bore's cross-section, the width of the prongs' cross-section when the prongs are together being closely accommodated by the depth of the bore's cross-section, such that when the sleeve is rotated, sides of the bore defining the depth of its cross-section bear against sides of the prongs defining the width of their cross-section to narrow the distance between the prongs until they are together.

* * * * *

UNITED STATES PATENT AND TRADEMARK OFFICE
CERTIFICATE OF CORRECTION

| | | |
|---|---|---|
| PATENT NO. | : 7,115,132 B2 | Page 1 of 1 |
| APPLICATION NO. | : 10/309585 | |
| DATED | : October 3, 2006 | |
| INVENTOR(S) | : Joseph P. Errico, Michael W. Dudasik and Rafail Zubok | |

It is certified that error appears in the above-identified patent and that said Letters Patent is hereby corrected as shown below:

On the Title Page, item [75], the city of residence for the 1st Inventor should read --Greenbrook-- not "Green Brook".

Signed and Sealed this

Twenty-first Day of August, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,115,132 B2 | Page 1 of 2 |
| APPLICATION NO. | : 10/309585 | |
| DATED | : October 3, 2006 | |
| INVENTOR(S) | : Joseph P. Errico, Michael W. Dudasik and Rafail Zubok | |

It is certified that error appears in the above-identified patent and that said Letters Patent is hereby corrected as shown below:

On the Title Page, section (63), please delete the text and insert the following:
-- continuation-in-part of U.S. Patent Application Serial Number 10/282,356 (filed October 29, 2002) entitled "Instrumentation and Methods For Use In Implanting an Artificial Intervertebral Disc", which is a continuation-in-part of U.S. Patent Application Serial Number 10/256,160 (filed September 26, 2002) entitled "Artificial Intervertebral Disc Having Limited Rotation Using a Captured Ball and Socket Joint With a Solid Ball and Compression Locking Post", which is a continuation-in-part of U.S. Patent Application Serial Number 10/175,417 (filed June 19, 2002) entitled "Artificial Intervertebral Disc Utilizing a Ball Joint Coupling", which is a continuation-in-part of U.S. Patent Application Serial Number 10/151,280 (filed May 20, 2002) entitled "Tension Bearing Artificial Disc Providing a Centroid of Motion Centrally Located Within an Intervertebral Space", which is a continuation-in-part of both U.S. Patent Application Serial Number 09/970,479 (filed October 4, 2001) entitled "Intervertebral Spacer Device Utilizing a Spirally Slotted Belleville Washer Having Radially Extending Grooves", now U.S. Patent No. 6,669,730 as well as U.S. Patent Application Serial Number 10/140,153 (filed May 7, 2002) entitled "Artificial Intervertebral Disc Having a Flexible Wire Mesh Vertebral Body Contact Element", the former being a continuation-in-part of U.S. Patent Application Serial Number 09/968,046 (filed October 1, 2001) entitled "Intervertebral Spacer Device Utilizing a Belleville Washer Having Radially Extending Grooves", now abandoned and the latter being a continuation-in-part of both U.S. Patent Application Serial Number 09/970,479 (detailed above) as well as U.S. Patent Application Serial Number 10/128,619 (filed April 23, 2002) entitled "Intervertebral Spacer Having a Flexible Wire Mesh Vertebral Body Contact Element", now U.S. Patent No. 6,863,689 which is a continuation-in-part of both U.S. Patent Application Serial Number 09/906,119 (filed July 16, 2001) and entitled "Trial Intervertebral Distraction Spacers", now U.S. Patent No. 6,607,559, as well as U.S. Patent Application Serial Number 09/982,148 (filed October 18, 2001) and

UNITED STATES PATENT AND TRADEMARK OFFICE
CERTIFICATE OF CORRECTION

PATENT NO. : 7,115,132 B2
APPLICATION NO. : 10/309585
DATED : October 3, 2006
INVENTOR(S) : Joseph P. Errico, Michael W. Dudasik and Rafail Zubok It is certified that error appears in the above-identified patent and that said Letters Patent is hereby corrected as shown below:

entitled "Intervertebral Spacer Device Having Arch Shaped Spring Elements", now U.S. Patent No. 6,673,113. All of the above mentioned applications are hereby incorporated by reference herein in their respective entireties. --

Signed and Sealed this

Twenty-first Day of April, 2009

JOHN DOLL
*Acting Director of the United States Patent and Trademark Office*